United States Patent [19]

Campbell et al.

[11] Patent Number: 4,483,859
[45] Date of Patent: Nov. 20, 1984

[54] 4-AMINO-6,7-DIMETHOXY-2-(4-HETEROARYL-PIPERAZINO) QUINAZOLINE ANTIHYPERTENSIVES

[75] Inventors: Simon F. Campbell, Deal; Rhona M. Plews, Canterbury, both of England

[73] Assignee: Pfizer Inc., New York, N.Y.

[21] Appl. No.: 526,005

[22] Filed: Aug. 24, 1983

Related U.S. Application Data

[62] Division of Ser. No. 333,672, Dec. 23, 1981, Pat. No. 4,435,401.

[30] Foreign Application Priority Data

Dec. 29, 1980 [GB] United Kingdom ............... 8041411

[51] Int. Cl.³ ............... A61K 31/495; A61K 31/505; C07D 401/00
[52] U.S. Cl. ................... 424/250; 424/251; 424/248.56; 544/62; 544/238; 544/119
[58] Field of Search .................... 544/238, 60; 424/248.56, 251, 250

[56] References Cited

U.S. PATENT DOCUMENTS 3,517,005 6/1970 Cronin .................... 544/292

FOREIGN PATENT DOCUMENTS 055583 12/1980 . European Pat. Off. ............ 544/198
2831112 2/1979 Netherlands ................... 424/251
2041932 9/1980 United Kingdom ............... 424/251

Primary Examiner—Paul M. Coughlan, Jr.
Assistant Examiner—Cecilia Shen
Attorney, Agent, or Firm—Connolly and Hutz

[57] ABSTRACT

2,4-Diaminoquinazoline compounds of the formula

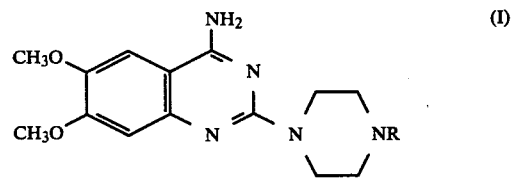

(I)

or a pharmaceutically acceptable salt thereof wherein R is a pyrimidinyl, pyrazinyl, pyridazinyl or triazinyl group linked to the piperazine ring by one of its carbon atoms, and optionally substituted by hydroxy, halogen, alkyl, aralkyl, alkoxy, aralkoxy, alkylthio, aryl, aryloxy and certain amino groups; their use as an antihypertensive agent and pharmaceutical compositions containing them.

9 Claims, No Drawings

4-AMINO-6,7-DIMETHOXY-2-(4-HETEROARYL-PIPERAZINO) QUINAZOLINE ANTIHYPERTENSIVES

CROSS REFERENCE TO RELATED APPLICATION

This application is a division of application Ser. No. 333,672 filed Dec. 23, 1981. Now U.S. Pat. No. 4,435,401, issued Mar. 6, 1984.

BACKGROUND OF THE INVENTION

1. Field of the Invention

This invention relates to therapeutic agents which are novel derivatives of 4-amino-6,7-dimethoxy-2-piperazinoquinazoline, their use as regulators of the cardiovascular system, particularly in the treatment of hypertension and pharmaceutical compositions containing them.

2. Description of the Prior Art

U.S. Pat. No. 3,511,836 discloses 4-amino-6,7-dimethoxyquinazolines and U.S. Pat. No. 3,669,968 discloses related 6,7,8-trimethoxyquinazolines of the formula

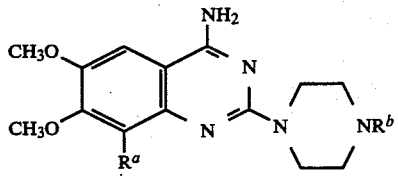

useful as antihypertensive agents, wherein $R^a$ is hydrogen or methoxy, respectively, and $R^b$ is inter alia, phenyl, benzyl, benzoyl, furoyl, thenoyl and pyridinecarbonyl. One of these compounds, 2-[4-(2-furoyl)piperazin-1-yl]-4-amino-6,7-dimethoxyquinazoline, is a clinically useful antihypertensive agent marketed under the generic name "prazosin".

U.S. Pat. No. 3,517,005 discloses antihypertensives including those of the formula

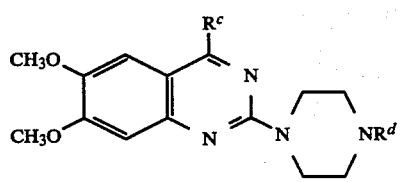

where $R^c$ is hydrogen or alkyl and $R^d$ is inter alia an aryl hydrocarbon moiety.

European Patent Application No. 22481 published Jan. 21, 1981 discloses antihypertensive agents of the formula

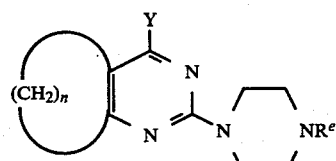

where n is 3, 4 or 5 and $R^e$ is, inter alia, a nitrogen-containing heterocyclic group, e.g., pyridyl, pyrimidinyl, quinolyl or quinazolyl; and Y is e.g. a substituted or unsubstituted amino group.

SUMMARY OF THE INVENTION

The present invention discloses new 4-amino-6,7-dimethoxyquinazolines of the formula

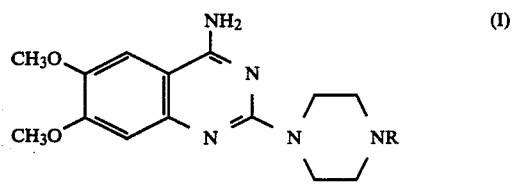

or a pharmaceutically acceptable acid addition salt thereof, wherein R is a nitrogen heterocyclic group linked to the piperazine ring by one of its carbon atoms, said heterocyclic group being a member selected from the group consisting of

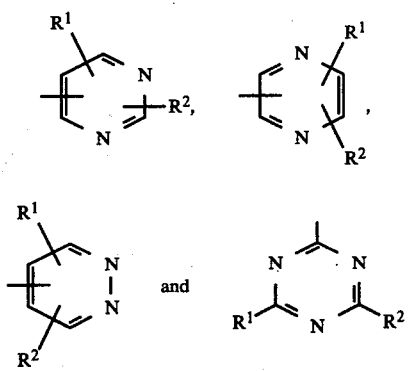

where $R^1$ is hydrogen and $R^2$ is 6,7-dimethoxy-1,2,3,4-tetrahydroisoquinolin-2-yl, or $R^1$ and $R^2$ are each a member selected from the group consisting of hydrogen, hydroxy, F, Cl, Br, I, (alk)$R^3$, O(alk) $R^3$, S(alk) $R^3$, $NR^4R^5$, $C_6H_4R^6$ and $OC_6H_4R^6$ and (alk) is ($C_1$–$C_4$) alkylene, $R^3$ is hydrogen or $C_6H_4R^6$, when taken separately, $R^4$ is hydrogen or ($C_1$–$C_4$) alkyl and $R^5$ is hydrogen, phenyl, (alk)$R^3$ or ($C_3$–$C_7$) cycloalkyl, or taken together with the nitrogen atom to which they are attached, $R^4$ and $R^5$ form a 1-pyrrolidinyl, piperidino, 4-methylpiperazino, morpholino, or thiomorpholino group, and $R^6$ is hydrogen, F, Cl, Br, I, ($C_1$–$C_4$) alkyl or ($C_1$–$C_4$) alkoxy.

Hydroxy substituted heterocyclic groups, R, may occur in tautomeric form. Such tautomers are within the scope of the invention.

Particularly preferred values of substituent R are the optionally substituted 2-pyrimidinyl, 4-pyrimidinyl, 1,3,5-triazin-2-yl, 3-pyridazinyl and 2-pyrazinyl moieties below

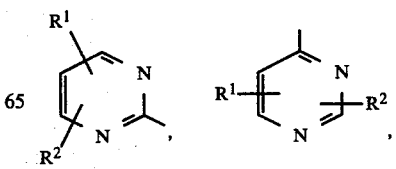

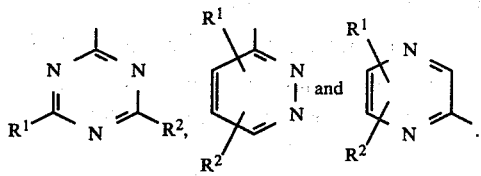

More particularly preferred compounds of the invention are those where R has one of the above values and:

a. one of $R^1$ and $R^2$ is hydrogen and the other is a member selected from the group consisting of hydroxy, Cl, Br, phenyl, phenoxy, (alk)$R^3$, O(alk)$R^3$, S(alk)$R^3$, $NR^4R^5$ and 6,7-dimethoxy-1,2,3,4-tetrahydroisoquinolin-2-yl, where $R^3$ is hydrogen, $R^4$ is hydrogen or ($C_1$-$C_4$) alkyl and $R^5$ is hydrogen, phenyl, ($C_5$-$C_6$) cycloalkyl or (alk)$R^3$ where $R^3$ is hydrogen, or $R^4$ and $R^5$ taken together with the nitrogen atom to which they are attached form a morpholino group; or b. $R^1$ and $R^2$ are the same and are each hydrogen, phenoxy, O(alk)$R^3$ or $NHR^5$ where $R^5$ is hydrogen or (alk)$R^3$, and $R^3$ is hydrogen.

Even more particularly preferred are those compounds of formula (I) wherein R has one of the values below.

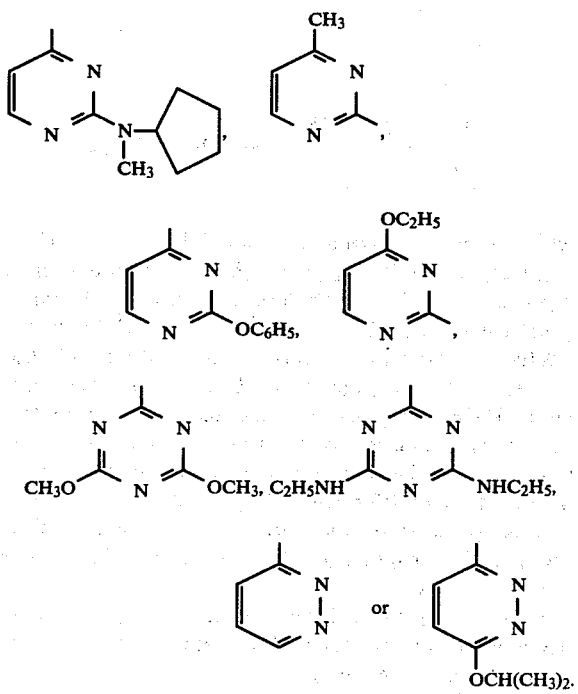

Pharmaceutically acceptable acid addition salts of the compounds of the invention are those formed from acids which form non-toxic acid addition salts containing pharmaceutically acceptable anions, such as the hydrochloride, hydrobromide, sulphate or bisulphate, phosphate or acid phosphate, acetate, maleate, fumarate, succinate, lactate, tartrate, citrate, glucconate, saccharate, mesylate and p-toluenesulphonate salts.

The compounds of formula (I) are valuable antihypertensive agents having significant advantages over the prior art.

DETAILED DESCRIPTION OF THE INVENTION

The compounds of the formula (I) can be prepared by reacting a quinazoline of the formula:

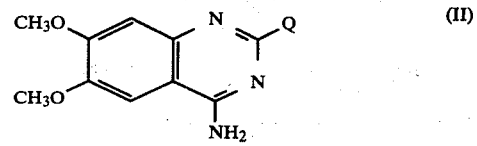

(II)

where Q is a facile leaving group, e.g., Cl, Br, $C_1$-$C_4$ alkoxy or $C_1$-$C_4$ alkylthio; with a piperazine of the formula:

(III)

where R is as previously defined. A particularly preferred value for Q is Cl.

In a typical procedure the reactants are heated together, e.g., at 70°–150° C., preferably under reflux, in a suitable solvent, e.g., r-butanol, for up to about 25 hours, the exact period of time of course depending on the nature of the reactants and the temperature employed, as will be known to those skilled in the art. The product can then be isolated and purified by conventional procedures.

If compound (III) is added in the form of an acid addition salt, then a tertiary amine base such as triethylamine is preferably added to the reaction mixture to release the free base of formula (III).

The starting materials of formula (III) are either known compounds or may be prepared by methods analogous to those of the prior art, many of such methods being illustrated in Preparations A to I. The starting quinazoline compounds of formula (II) are well known in the art; see e.g., U.S. Pat. No. 3,511,836.

The compounds of the formula (I) can also be prepared by reacting a 2-piperazinoquinazoline of the formula:

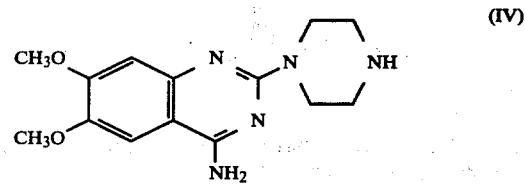

(IV)

with a heterocycle of the formula:

R—Q    (V)

where
R and Q are as previously defined and
Q is preferably Cl.

The reaction may be carried out in a similar manner to the previous method. Similarly, the product may be isolated and purified by conventional procedure. The starting materials of the formula (V) are either known compounds of may be prepared by methods analogous to those of the prior art. The starting 2- piperazinoquinazoline (IV) is provided, for example, in U.S. Pat. No. 3,511,836.

Some of the compounds of the formula (I) can be prepared from other compounds of the formula (I). For example, compounds of the formula (I) in which R contains NR$^4$R$^5$, where R$^4$ and R$^5$ are as defined for formula (I), can be prepared by reacting the corresponding compound in which R is a halogen substituted moiety with the appropriate amine of the formula R$^4$R$^5$NH. Generally, fairly vigorous reaction conditions are necessary, e.g., heating the reactants in a suitable solvent, e.g., n-butanol, at up to 180° C. in a bomb, for up to about 48 hours. A preferred halogen substituent is chloro.

Requisite starting compounds R Q, as defined above, are either known compounds or are prepared by analogous methods well known to those of skill in the art, see for example, "Comprehensive Organic Chemistry", by Barton and Ollis, Pergamon Press, New York, N.Y., Vol. 4, 1979, pp. 85-103 and 145-153 and references cited therein.

The pharmaceutically acceptable acid addition salts of the compounds of the formula (I) can be prepared by conventional procedures, e.g., by reacting the free base with the appropriate acid in an inert organic solvent, and collecting the resulting precipitate of the salt by filtration. If necessary, the product may then be recrystallized to purify it.

The antihypertensive activity of the compounds of the formula (I) is shown by their ability to lower the blood pressure of conscious spontaneously hypertensive rats and conscious renally hypertensive dogs, when administered orally at doses of up to 5 mg/kg.

The compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally, for example, intramuscularly, intravenously or subcutaneously. For parenteral administration, they are best used in the form of a sterile aqueous solution which may contain other solutes, for example, enough salts or glucose to make the solution isotonic.

Thus the invention also provides a pharmaceutical composition comprising an antihypertensive effective amount of a compound of the formula (I) or pharmaceutically acceptable acid addition salt thereof together with a pharmaceutically acceptable diluent or carrier.

The invention further provides a compound of the formula (I) or a pharmaceutically acceptable acid addition salt thereof, for use in treating hypertension in mammals, including humans.

The compounds of the invention can be administered to mammals, including humans, for the treatment of hypertension by either the oral or parenteral routes, and may be administered orally at dosage levels approximately within the range 1 to 20 mg/day for an average adult patient (70 kg) given in a single dose or up to 3 divided doses. Intravenous dosage levels would be expected to be about 1/5 to 1/10th of the daily oral dose. Thus for an average adult patient, individual oral doses in tablet or capsule form will be approximately in the range from ⅓ to 20 mg of the active compound. Variations will necessarilly occur depending on the weight and condition of the subject being treated and the particular route of administration chosen as will be known to those skilled in the art.

The invention yet further provides a method of treating a mammal, including a human being, having hypertension, which comprises administering to the mammal an antihypertensive amount of a compound of the formula (I) or pharmaceutically acceptable acid addition salt thereof or pharmaceutical composition as defined above.

The invention is illustrated by the following Examples, in which all temperatures are in °C.

EXAMPLE 1

4-Amino-6,7-dimethoxy-2-[4-(4-phenylpyrimidin-2-yl)piperazino] quinazoline, hemihydrate

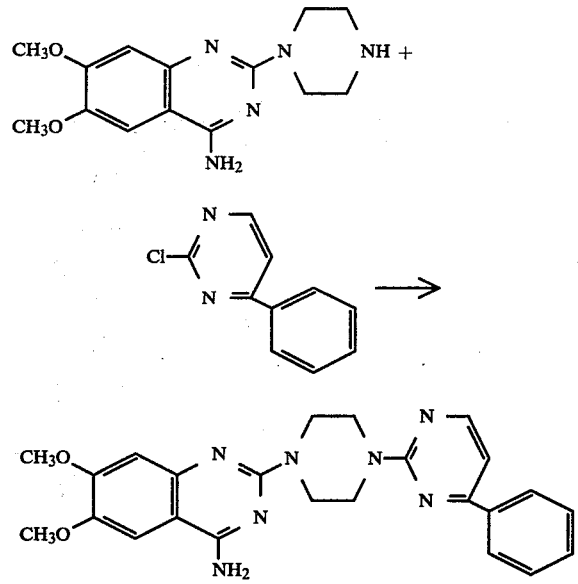

4-Amino-6,7-dimethoxy-2-piperazino-quinazoline (3.44 g, 0.012 mole) and 2-chloro-4-phenylpyrimidine (2.5 g, 0.011 mole) [J. Chem. Soc., 2328 (1951)] in n-butanol (250 ml) were heated under reflux for six hours. After cooling the solid product was collected, washed with diethylether, and partitioned between chloroform and saturated aqueous sodium carbonate solution. The chloroform layer was separated, the aqueous layer extracted with chloroform and the combined chloroform layers were washed with water, dried (Na$_2$SO$_4$) and evaporated in vacuo. The residue (5 g) was chromatographed on silica eluting with chloroform and chloroform-methanol (97.5:2.5 by volume). Appropriate fractions were combined, evaporated and the resulting solid crystallized from dimethylformamide (DMF)/diethyl ether to give 4-amino-6,7-dimethoxy-2-[4-(4-phenylpyrimidin-2-yl)-piperazino] quinazoline hemihydrate, (2.28 g), m.p. 250° C. (dec).

Analysis %: Found: C, 63.5; H, 5.8; N, 21.8. Calculated for C$_{24}$H$_{25}$N$_7$O$_2$.½H$_2$O: C, 63.7; H, 5.8; N, 21.7.

The following Examples were carried out in the same general manner as Example 1, but in some cases the reaction mixture was evaporated in vacuo and then purified as described. Other modifications were as follows. In Example 4 the product from chromatography was converted to the dihydrochloride in the standard manner, using hydrogen chloride in a suitable solvent. In Example 5, the product was collected from the cooled reaction mixture then recrystallized from ethanol. In Examples 7, 8, 14 and 18, the initial reaction was carried out in ethanol and in Examples 8 and 14 the products, after chromatography, were converted to the dihyrochloride salts. In Example 10, the product from chromatography was further purified by preparative high pressure liquid chromatography (HPLC). In Examples 11 and 12, after basification and extraction, the residue was recrystallized from methanol. In Example 13, the solid product from the reaction mixture was taken up in DMF/diethyl ether and precipitated with water. In Example 15, the product from chromatography was converted to the citrate salt using citric acid in a suitable solvent, recrystallized from methanol, basified, then treated with maleic acid, and the maleate salt recrystallized from methanol.

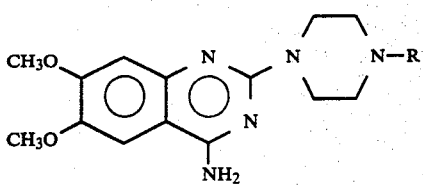

| Example No. | R | Form Isolated and m.p. °C | Analysis % (calculated figures in brackets) | | |
|---|---|---|---|---|---|
| | | | C | H | N |
| 2 | N≡/N, OCH3 | Free base 202–203° | 57.1 (57.4 | 6.0 5.8 | 25.1 24.7) |
| 3 | N≡/N, O-phenyl | hemihydrate 191–192° | 61.6 (61.5 | 5.6 5.6 | 20.5 20.9) |
| 4 | N≡/N, NH2 | dihydrochloride 2½ H2O 245–248° | 43.5 (43.2 | 5.1 5.8 | 22.3 22.4) |
| 5 | N≡/N, N(CH3)2 | hydrochloride ¼ H2O 262–264° | 52.2 (52.2 | 6.2 6.2 | 24.4 24.3) |
| 6 | N≡/N, CH3 | ⅓ ethanolate 225–226° | 59.2 (59.5 | 6.2 6.4 | 24.9 24.7) |
| 7 | N≡/N, OCH2CH3 | free base 227° | 58.5 (58.4 | 6.4 6.1 | 23.4 23.8) |

-continued

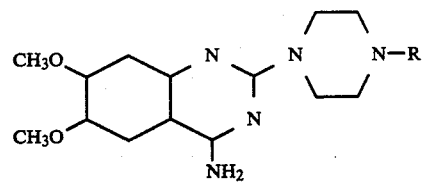

| Example No. | R | Form Isolated and m.p. °C. | Analysis % (calculated figures in brackets) | | |
|---|---|---|---|---|---|
| | | | C | H | N |
| 8 | 2-methyl-4-(O(CH₂)₂CH₃)pyrimidin-yl | dihydrochloride hydrate 265–269° | 48.9 (48.8 | 5.6 6.1 | 19.0 19.0) |
| 9 | 2,6-dimethoxy-4-methylpyrimidin-yl (OCH₃, OCH₃) | free base 194–195° | 56.0 (56.2 | 5.9 5.9 | 23.2 22.9) |
| 10 | 2,6-diphenoxy-4-methylpyrimidin-yl | free base 145–150° | 61.9 (62.0 | 5.1 5.2 | 19.9 20.0) |
| 11 | 2,6-bis(NHCH₂CH₃)-4-methylpyrimidin-yl | free base 130–133° | 55.1 (55.5 | 6.7 6.7 | 30.8 30.8) |
| 12 | 2,6-diamino-4-methylpyrimidin-yl | free base hydrate 276–177° | 48.9 (49.0 | 5.6 5.8 | 33.4 33.6) |
| 13 | 2,6-dimethoxy-pyrimidin-yl (OCH₃, OCH₃) | hydrochloride hydrate 225–226° | 46.9 (47.3 | 5.7 5.6 | 23.1 23.3) |
| 14 | 2-methyl-4-phenoxypyrimidin-yl | dihydrochloride 267–268° | 54.3 (54.1 | 5.3 5.1 | 18.4 18.4) |

-continued

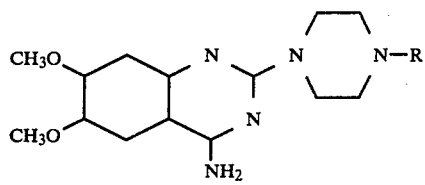

| Example No. | R | Form Isolated and m.p. °C. | Analysis % (calculated figures in brackets) | | |
|---|---|---|---|---|---|
| | | | C | H | N |
| 15 | (pyrimidinyl-tetrahydroisoquinoline with OCH₃ groups) | dimaleate hydrate 224–226° | 55.3 (54.9 | 5.2 5.5 | 13.7 13.9) |
| 16 | (pyrimidinyl-N(CH₃)₂) | free base ½ mole EtOAc hemihydrate 187–188° | 57.2 (57.0 | 6.7 6.7 | 24.2 24.2) |
| 17 | (pyrimidinyl-OCH(CH₃)₂) | free base 263–265° | 59.3 (59.3 | 6.6 6.4 | 23.3 23.1) |
| 18 | (pyrimidinyl-OCH₂CH₂CH₃) | free base hemihydrate 239–241° | 58.5 (58.1 | 6.4 6.5 | 22.8 22.6) |
| 19 | (pyrimidinyl-SCH₃) | free base 238–239° | 54.9 (55.2 | 5.5 5.6 | 23.4 23.7) |

EXAMPLE 20

4-Amino-6,7-dimethoxy-2-[4-(2-phenoxypyrimidin-4-yl)piperazino] quinazoline ¾ hydrate

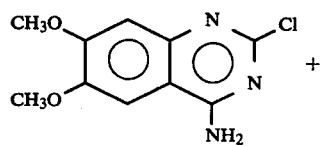

+

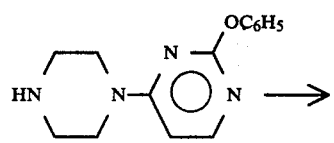

→

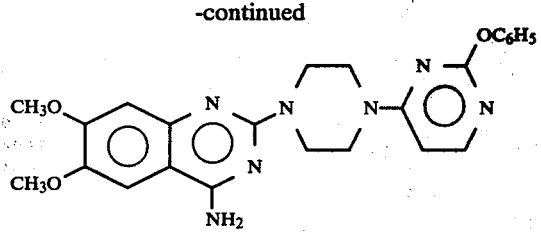

4-Amino-2-chloro-6,7-dimethoxyquinazoline (0.8 g, 3.3 mmole) and 2-phenoxy-4-piperazinopyrimidine dihydrochloride (1.2 g, 3.6 mmole) were heated under reflux in n-butanol (50 ml) overnight. The mixture was then evaporated in vacuo and the residue partitioned between chloroform/methanol/saturated aqueous sodium carbonate solution (300 ml:100 ml:50 ml). The chloroform/methanol layer was separated, dried (Na₂SO₄), evaporated in vacuo then the residue (1 g) chromatographed on silica gel (85 g). The column was eluted with chloroform, then chloroform containing 2.5% methanol by volume, appropriate fractions combined, evaporated in vacuo and the residue recrystallized from ethanol to give the title compound, (0.14 g) m.p. 253°–254° C.

Analysis %: Found: C, 60.8; H, 5.5; N, 20.7. Calculated for $C_{24}H_{25}N_7O_3.\frac{3}{4}H_2O$: C, 60.9; H, 5.7; N, 20.7.

The following compounds were prepared by the procedure of Example 20, except that in some cases triethylamine was included in the reaction mixture and other modifications were as follows:

In Example 21, the reaction mixture was evaporated, the residue partitioned between chloroform/water, the solid collected, boiled with methanol, filtered and the filtrate evaporated. The residue was then purified by chromatography. In Example 22 the reaction mixture was evaporated in vacuo and the residue crystallized from methanol/diethyl ether; in Example 24 cooling of the reaction mixture yielded 4-amino-2-dimethylamino-6,7-dimethoxyquinazoline formed due to inadvertent presence of dimethylamine in the piperazino starting material. The mother liquors were treated as in the general example, then the product from chromatography purified by preparative high pressure liquid chromatography and converted to the maleate salt in the standard manner using maleic acid in a suitable solvent. In Example 27, the solid product was collected from the cooled reaction mixture and was recrystallized from dimethylformamide/diethyl ether. In Example 28, the solid product was collected, recrystallized from methanol then converted to the hydrochloride salt in the standard manner using hydrogen chloride in a suitable solvent. In Example 29 the solid product was collected and recrystallized from dimethylformamide. In Example 30 the product from chromatography was converted to the maleate salt using maleic acid which salt was crystallized from methanol. In Example 31 the solid product was collected then washed with diethyl ether.

| Example No. | R | Form Isolated and m.p., °C | Analysis % (Theoretical in brackets) C | H | N |
|---|---|---|---|---|---|
| 21 | 2-pyrimidinyl | dihydrochloride 265–266° | 49.0 (49.1 | 5.3 5.3 | 22.5 22.3) |
| 22 | 2-(dimethylamino)pyrimidin-4-yl | dihydrochloride dihydrate 255–265° | 46.2 (46.2 | 5.8 6.2 | 21.8 21.6) |
| 23 | 2-hydroxypyrimidin-4-yl | free base ¼ hydrate 265° | 54.5 (54.5 | 5.4 5.7 | 24.9 24.7) |
| 24 | 6-dimethylaminopyridazin-3-yl | dimaleate hemihydrate 203–204° | 51.5 (51.6 | 5.4 5.4 | 17.4 17.2) |
| 25 | 6-phenoxypyridazin-3-yl | free base 270–272° | 62.8 (62.7 | 5.6 5.5 | 21.2 21.3) |
| 26 | 6-dimethoxymethylpyridazin-3-yl | free base 247–248° | 59.1 (59.3 | 6.6 6.4 | 22.7 23.1) |

-continued

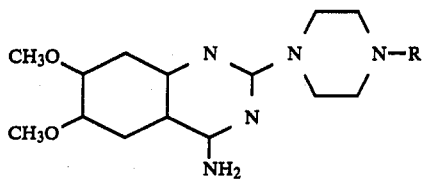

| Example No. | R | Form Isolated and m.p., °C. | Analysis % (Theoretical in brackets) | | |
|---|---|---|---|---|---|
| | | | C | H | N |
| 27 | ![N—N ring with OCH3] | free base 285–287° | 57.3 (57.4 | 6.0 5.8 | 24.9 24.7) |
| 28 | ![N—N ring with phenyl] | dihydrochloride 1¾ hydrate 266–268° | 52.4 (52.6 | 5.5 5.6 | 18.3 17.9) |
| 29 | ![N—N ring] | hydrochloride sesquihydrate 214–215° | 50.6 (50.2 | 5.4 5.9 | 22.4 22.8) |
| 30 | ![N ring with OCH2CH3 groups] | maleate hydrate 247–248° | 50.6 (50.8 | 5.5 5.8 | 19.0 19.0) |
| 31 | ![N ring] | hydrochloride 291–293° | 53.2 (58.5 | 5.6 5.5 | 24.5 24.3) |

EXAMPLE 32

4-Amino-6,7-dimethoxy-2-[4-(6-hydroxypyridazin-3-yl)piperazino] quinazoline

Triethylamine (2.5 g, 0.025 mole) and 4-(6-hydroxypyridazin-3-yl)piperazine hydrobromide (2.7 g, 0.011 mole) in n-butanol (150 ml) were heated to reflux, then filtered and 4-amino-2-chloro-6,7-dimethoxyquinazoline (2.4 g, 0.010 mole) added to the filtrate. The mixture was heated under reflux for three hours then left at room temperature for 66 hours. The solid product was collected, washed with diethyl ether, then slurried in hot methanol (50 ml), filtered and washed again with hot methanol followed by hot isopropanol. A slurry of the product in aqueous methanol (methanol:water 1:3 by volume) was basified to pH 12 with dilute ammonium hydroxide and extracted with chloroform (100 ml) followed by chloroform-methanol (95:5; 3×100 ml). The combined organic layers were dried (Na2SO4) and evaporated in vacuo to give a solid (0.6 g). The aqueous fraction was filtered and the solid washed with water and dried to give a further 1.6 g of solid product identical when analyzed by thin layer chromatography to the first solid. The two solids were combined then recrystallized from dimethylformamide/diethyl ether and the resulting solid washed with diethyl ether, hot isopropanol and diethyl ether again to give 4-amino-6,7-dimethoxy-2-[4-(6-hydroxypyridazin-3-yl)piperazino] quinazoline (1.3 g), m.p. 296°–297° C.

Analysis %: Found: C, 55.9; H, 5.7; N, 25.2. Calculated for $C_{18}H_{21}N_7O_3$: C, 56.4; H, 5.5; N, 25.6.

EXAMPLE 33

4-Amino-6,7-dimethoxy-2-[4-(6-chloropyridazin-3-yl)piperazino] quinazoline

4-Amino-6,7-dimethoxy-2-piperazinoquinazoline (3.0 g, 10.4 mmole), 3-chloro-6-methoxy-pyridazine (3.96 g, 27.4 mmole) and triethylamine (5.0 g, 49.5 mmole) in n-pentanol (210 ml) were heated under reflux for 25 hours. The solvent was evaporated in vacuo and the residue partitioned between chloroform and saturated aqueous sodium carbonate solution. The organic layer was separated, washed with water, dried (Na2SO4) and evaporated in vacuo. The residue was chromatographed on silica gel (200 g) eluting with chloroform followed by 5% methanol in chloroform. Further purification of the major product by HPLC using a Waters 500 Prep. LC/system, eluting with 6% by volume methanol in methylene chloride at a flow rate of 0.15 liters per minute gave the desired product which was recrystallized from methanol, m.p. 269°–270° C. (0.5 g).

Analysis %: Found: C, 53.7; H, 4.9; N, 24.2. Calculated for $C_{18}H_{20}ClN_7O_2$: C, 53.8; H, 5.0; N, 24.4.

EXAMPLE 34

4-Amino-6,7-dimethoxy-2-[4-(2-chloropyrimidin-4-yl)piperazino] quinazoline

4-Amino-6,7-dimethoxy-2-piperazino-quinazoline (30.0 g, 0.104 mole), 2,4-dichloropyrimidine (17.3 g, 0.117 mole) and triethylamine (20.5 g, 0.203 mole) in ethanol (1200 ml) were heated at reflux for three hours. The solid which separated on cooling was filtered, slurried in hot isopropanol (500 ml), filtered and washed with hot methanol. The product was partitioned between 5% by volume methanol in methylene chloride and 10% (w/w) aqueous sodium carbonate solution, the organic layer separated, washed with water, dried ($Na_2SO_4$) and evaporated in vacuo. The resulting solid was slurried in hot isopropanol, filtered and washed with hot isopropanol to afford 20 g. of the title compound, m.p. 266° C.

Analysis %: Found: C, 53.75; H, 5.0; N, 24.7. Calculated for $C_{18}H_{20}ClN_7O_2$: C, 53.8; H, 5.0; N, 24.4.

EXAMPLE 35

Employing the above methods with the appropriate starting materials in each case, the following compounds are obtained in like manner.

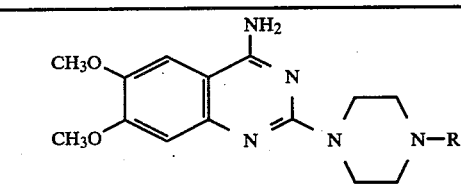

| R |
|---|
| 1,3,5-triazin-2-yl |
| 4-(p-Fluorophenyl)pyrimidin-2-yl |
| 4-(m-Iodophenyl)pyrimidin-2-yl |
| 2-(o-Methylphenyl)pyrimidin-4-yl |
| 2-(p-Isopropylphenyl)pyrimidin-4-yl |
| 2-(m-t-Butylphenyl)pyrimidin-4-yl |
| 2-(p-t-Butoxyphenyl)pyrimidin-4-yl |
| 4-(m-Ethoxyphenyl)pyrimidin-2-yl |
| 4-(o-Methoxyphenyl)pyrimidin-2-yl |
| 4-Phenoxypyrimidin-2-yl |
| 4-(p-Chlorophenoxy)pyrimidin-2-yl |
| 4-(o-Bromophenoxy)pyrimidin-2-yl |
| 2-(m-Fluorophenoxy)pyrimidin-4-yl |
| 2-(p-Methylphenyl)pyrimidin-4-yl |
| 2-(p-Ethylphenyl)pyrimidin-4-yl |
| 4-(o-Isopropylphenyl)pyrimidin-2-yl |
| 4-(o-Methoxyphenyl)pyrimidin-2-yl |
| 4-n-Propylpyrimidin-2-yl |
| 6-sec-Butylpyrimidin-4-yl |
| 6-Benzylpyrimidin-4-yl |
| 4-(2-Phenylethyl)-pyrimidin-2-yl |
| 4-[2-(p-Fluorophenyl)ethyl]pyrimidin-2-yl |
| 4-[3-(m-Chlorophenyl)propyl]pyrimidin-2-yl |
| 2-[2-(p-Methylphenyl)propyl]pyrimidin-4-yl |
| 2-[3-(o-Ethoxyphenyl)propyl]pyrimidin-4-yl |
| 4-[3-(p-t-Butoxyphenyl)propyl]pyrimidin-2-yl |
| 4-[3-(m-n-Butylphenyl)propyl]pyrimidin-2-yl |
| 4-[4-(p-Bromophenyl)butyl]pyrimidin-2-yl |
| 4-[3-(p-Iodophenyl)butyl]pyrimidin-2-yl |
| 2-[4-(phenylbutyl]pyrimidin-4-yl |
| 4-Benzyloxypyrimidin-2-yl |
| 4-(p-Chlorophenyl)methylpyrimidin-2-yl |
| 2-Ethoxypyrimidin-4-yl |
| 4-Isopropoxypyrimidin-2-yl |
| 4-n-Butoxypyrimidin-2-yl |
| 4-[2-(m-Bromophenyl)ethoxy]pyrimidin-2-yl |
| 2-[1-(p-Methoxyphenyl)ethoxypyrimidin-4-yl |
| 2-[3-(o-Ethylphenyl)propoxypyrimidin-4-yl |
| 2-[4-(p-Fluorophenyl)butoxypyrimidin-4-yl |
| 4-Methylthiopyrimidin-2-yl |

-continued

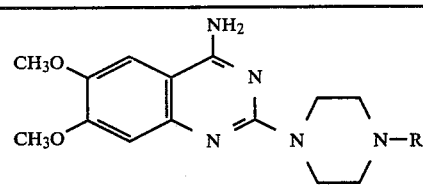

| R |
|---|
| 4-Isopropylthiopyrimidin-2-yl |
| 2-n-Butylthiopyrimidin-4-yl |
| 2-Benzylthiopyrimidin-4-yl |
| 6-(2-Phenylethylthio)pyrimidin-4-yl |
| 4-[4-(p-Chlorophenyl)butylthio] pyrimidin-2-yl |
| 4-[3-(m-Methoxyphenyl)propylthio]pyrimidin-2-yl |
| 4-Aminopyrimidin-2-yl |
| 4-Methylaminopyrimidin-2-yl |
| 4-n-Propylaminopyrimidin-2-yl |
| 6-n-Butylaminopyrimidin-4-yl |
| 6-Phenylaminopyrimidin-4-yl |
| 2-Benzylaminopyrimidin-4-yl |
| 4-(2-Phenylethyl)aminopyrimidin-2-yl |
| 4-(3-p-Chlorophenylpropyl)aminopyrimidin-2-yl |
| 4-N—Methyl-N—ethylaminopyrimidin-2-yl |
| 6-N—Phenyl-N—propylaminopyrimidin-4-yl |
| 6-N—Ethyl-N—sec-butylaminopyrimidin-4-yl |
| 4-N—Methyl-N—[4-(p-chlorophenyl)butyl]pyrimidin-2-yl |
| 4-Cycloheptylaminopyrimidin-2-yl |
| 4-Cyclohexylaminopyrimidin-2-yl |
| 2-N—Cyclopropyl-N—methylpyrimidin-4-yl |
| 2-N—Cyclobutyl-N—ethylpyrimidin-4-yl |
| 6-N—Cyclopentyl-N—isopropylpyrimidin-4-yl |
| 4-Morpholinopyrimidin-2-yl |
| 2-Thiomorpholinopyrimidin-4-yl |
| 2-[1-pyrrolidinyl]pyrimidin-4-yl |
| 6-Piperidinopyrimidin-4-yl |
| 6-(4-Methylpiperazino)pyrimidin-4-yl |
| 6-Benzylpyridazin-3-yl |
| 6-Fluoropyridazin-3-yl |
| 6-Bromopyridazin-3-yl |
| 6-(p-Bromophenyl)pyridazin-3-yl |
| 6-(o-Methylphenyl)pyridazin-3-yl |
| 6-(p-t-Butoxyphenyl)pyridazin-3-yl |
| 6-(m-Methoxyphenyl)pyridazin-3-yl |
| 6-(p-Chlorophenoxy)pyridazin-3-yl |
| 6-(p-Ethylphenoxy)pyridazin-3-yl |
| 6-(p-Ethoxyphenoxy)pyridazin-3-yl |
| 6-Methylpyridazin-3-yl |
| 6-Ethylpyridazin-3-yl |
| 6-Aminopyridazin-3-yl |
| 6-Methylaminopyridazin-3-yl |
| 5,6-Dimethylpyridazin-3-yl |
| 5-Amino-6-methoxypyridazin-3-yl |
| 5-Amino-6-ethoxypyridazin-3-yl |
| 5-Chloro-6-methoxypyridazin-3-yl |
| 6-Methylaminopyridazin-4-yl |
| 6-Chloro-5-ethylpyridazin-3-yl |
| 6-Chloro-5-methylpyridazin-3-yl |
| 6-Amino-5-methylpyridazin-3-yl |
| 4,6-Dimorpholino-1,3,5-triazin-2-yl |
| 6-Ethoxy-5-methylpyrazin-2-yl |
| 6-Ethoxypyrazin-2-yl |
| 5-Ethyl-6-methoxypyrazin-2-yl |
| 5,6-Dimethylpyrazin-2-yl |
| 6-Methylpyrazin-2-yl |
| 6-n-Butylpyrazin-2-yl |
| 6-isopropylpyrazin-2-yl |
| 5-Ethoxypyrazin-2-yl |
| 5-Methoxypyrazin-2-yl |
| 5-Dimethylamino-6-methylpyrazin-2-yl |
| 5-Morpholino-6-ethylpyrazin-2-yl |
| 5-n-Butyl-6-Methylaminopyrazin-2-yl |
| 5,6-Diethylpyrazin-2-yl |
| 5-Amino-6-methylpyrazin-2-yl |
| 5-Aminopyrazin-2-yl |

EXAMPLE 36

4-Amino-6,7-dimethoxy-2-[4-(2-morpholinopyrimidin-4-yl)-piperazino] quinazoline 4-Amino-6,7-dimethoxy-2-[4-(2-chloropyrimidin-4-yl)-piperazino] quinazoline (2.0 g, 5.0 mmole) and morpholine (1.1 g, 12.6 mmole) in n-butanol (150 ml) were heated in a bomb at 160° C. for 19 hours. The solvent was evaporated in vacuo and the residue partitioned between 5% methanol in chloroform and 5N sodium hydroxide solution. The organic layer was separated, washed with water, dried (Na2SO4) and evaporated in vacuo. The residue was chromatographed on silica gel (20 g, "Kieselgel" (Trade Mark) 60H) eluting with chloroform. Appropriate fractions were combined and evaporated in vacuo. Crystallization from ethyl acetate gave 0.8 g of the desired product, m.p. 232°–233° C.

Analysis %: Found: C, 58.0; H, 6.3; N, 24.9. Calculated for $C_{22}H_{28}N_8O_3$: C, 58.4; H, 6.2; N, 24.8.

EXAMPLE 37

4-Amino-6,7-dimethoxy-2-[4-(2-{N-cyclopentyl-N-methylamino}pyrimidin-4-yl)piperazino] quinazoline was prepared in a manner similar to that of Example 36, starting from the product of Example 34 and N-cyclopentylmethylamine, but a temperature of 180° for 48 hours was required. The product was characterized as the dihydrochloride dihydrate, m.p. 333°–4° C.

Analysis %: Found: C, 50.0; H, 6.2; N, 19.8. Calculated for $C_{24}H_{32}N_8O_2.2HCl.2H_2O$: C, 50.3; H, 6.7; N, 19.5.

EXAMPLE 38

4-Amino-6,7-dimethoxy-2-[4-(2-N-methylanilino-pyrimidin-4-yl)piperazino] quinazoline, m.p. 252°–3° C., was prepared in a manner similar to Example 36, starting from the product of Example 34 and N-methylaniline.

Analysis %: Found: C, 63.4; H, 6.0; N, 23.8. Calculated for $C_{25}H_{28}N_8O_2$: C, 63.5; H, 6.0; N, 23.7.

EXAMPLE 39

In like manner the following products are prepared by the method of Examples 36–38 as outlined below

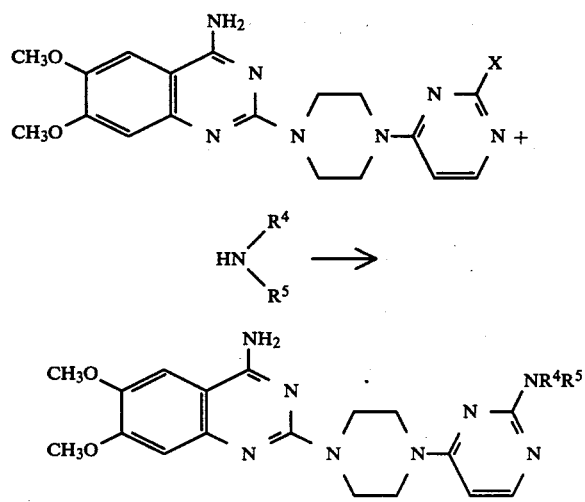

where X is Cl or Br and $R^4$ and $R^5$ are as defined below.

| $R^4$ | $R^5$ |
| --- | --- |
| H | CH3 |
| H | C2H5 |
| H | CH(CH3)2 |
| H | (CH2)3CH3 |
| H | CH2CH(CH3)2 |
| H | C6H5 |
| H | cyclopropyl |
| H | cyclopentyl |
| H | cyclohexyl |
| H | cycloheptyl |
| CH3 | C2H5 |
| C2H5 | C2H5 |
| n-C3H7 | C2H5 |
| n-C3H7 | n-C4H9 |
| n-C4H9 | n-C4H9 |
| CH3 | cyclopropyl |
| C2H5 | cyclobutyl |
| n-C3H7 | cyclopentyl |
| CH3 | cyclohexyl |
| H | benzyl |
| H | 2-phenylethyl |
| CH3 | 3-phenylpropyl |
| C2H5 | 3-phenylbutyl | or $R^4 + R^5 + N$ is:
thiomorpholin,
piperidino
4-methylpiperazino

EXAMPLE 40

By employing a compound of formula (I) where R is 4-halo-1,3,5-triazin-2-yl or 4,6-dihalo-1,3,5-triazin-2-yl, the following compounds are obtained by the methods of Examples 36–38, where halo is Cl or Br.

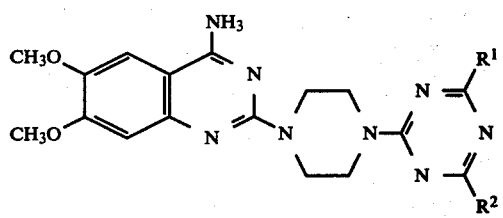

where $R^1$ is hydrogen or $NR^4R^5$ and $R^2$ is $NR^4R^5$ where $R^4$ and $R^5$ are as defined in Example 39.

EXAMPLE 41

To a solution of 2.0 mmole 4-amino-6,7-dimethoxy-2-[4-(2-chloropyrimidin-4-yl)-piperazino] quinazoline in n-butanol is added 20 ml of 0.1N hydrogen chloride in butanol. The resulting mixture is stirred for a few minutes, the solvent evaporated in vacuo to a small volume and the residue treated with ethyl ether to complete the precipitation of the hydrochloride salt.

In similar manner the remaining compounds of formula (I) are converted to hydrochloride salts.

When the hydrogen chloride employed above is replaced by one of the following acids the corresponding salts are obtained in like manner:

hydrogen bromide, hydrogen iodine, sulfuric acid, ammonium bisulfate, phosphoric acid, potassium dihydrogen phosphate, acetic acid, maleic acid, fumaric acid, succinic acid, lactic acid, tartaric acid, citric acid, gluconic acid, saccharic acid, methylsulfonic acid and p-toluenesulfonic acid.

PREPARATION A

2-Phenoxy-4-piperazinopyrimidine i. 2-Chloro-4-(4-formylpiperazino)pyrimidine 1-Formylpiperazine (38.5 g) and triethylamine (34 g) in ethanol (500 ml) were added slowly to a stirred solution of 2,4-dichloropyrimidine (50 g) in ethanol (2.5 ml) at room temperature. The mixture was stirred at room temperature for 24 hours then evaporated in vacuo and the residue partitioned between chloroform and water. The organic phase was washed with water and the combined aqueous phases extracted with chloroform. The combined chloroform extracts were dried (Na$_2$SO$_4$), evaporated in vacuo and the residue was crystallized twice from ethyl acetate to give 2-chloro-4-(4-formylpiperazino)pyrimidine, (24 g), m.p. 125°–126° C.

Analysis %: Found: C, 47.5; H, 4.8; N, 24.4. Calculated for C$_9$H$_{11}$ClN$_4$O: C, 47.7; H, 4.9; N, 24.7.

A further 6.0 g of product was obtained on evaporation of the ethyl acetate to half volume and cooling.

ii. 2-Phenoxy-4-(4-formylpiperazino)pyrimidine ¼ hydrate

Phenol (2.07 g) was added to a solution of sodium methoxide (from 0.51 g sodium) in dry methanol (20 ml) then the solvent was evaporated in vacuo. The sodium phenoxide residue in 1,2-dimethoxyethane (160 ml) was treated with 2-chloro-4-(4-formylpiperazino)pyrimidine (5.0 g) and heated under reflux for 24 hours. The solvent was evaporated in vacuo and the residue partitioned between chloroform (50 ml) and water (30 ml). The aqueous layer was extracted with chloroform and the combined chloroform extracts were dried (Na$_2$SO$_4$) and evaporated in vacuo. The residue was triturated with diethyl ether and the resulting solid re-crystallized from ethyl acetate to give 2-phenoxy-4-(4-formylpiperazino)pyrimidine ¼ hydrate (2.93 g) m.p. 149°–151° C.

Analysis %: Found: C,62.0; H,5.8; N,19.7. Calculated for C$_{15}$H$_{16}$N$_4$O$_2$.¼H$_2$O: C,62.4; H,5.8; N,19.4.

iii. 2-Phenoxy-4-piperazinopyrimidine

2-Phenoxy-4-(4-formylpiperazino)pyrimidine (2.6 g) in methanol (27 ml) and 2N hydrochloric acid (6.9 ml) was left at room temperature for 24 hours and then heated on a steam bath for 30 minutes. The solvent was evaporated in vacuo and the residue re-crystallized twice from isopropanol to give 2-phenoxy-4-piperazinopyrimidine (1.5 g) characterized spectroscopically, and used directly.

PREPARATION B

2-dimethylamino-4-piperazinopyrimidine, dihydrochloride ¾ hydrate

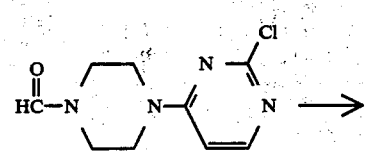

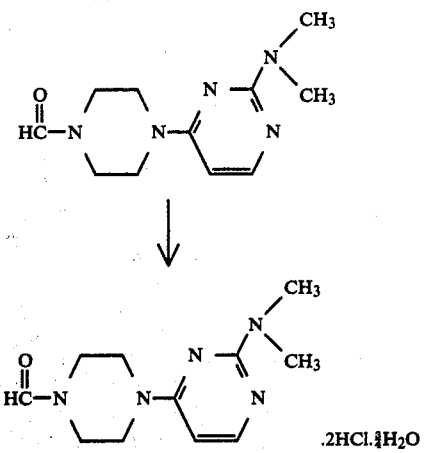

i. 2-Chloro-4-(4-formylpiperazino)pyrimidine (5.0 g) and dimethylamine (7.8 ml, 33% solution in ethanol) in ethanol (70 ml) were heated under reflux for 8 hours. The solvent was evaporated in vacuo and the residue was partitioned between chloroform and water. The aqueous layer was extracted twice with chloroform and the combined chloroform layers dried (Na$_2$SO$_4$) and evaporated in vacuo. The residue was re-crystallized from ethyl acetate to give 2-dimethylamino-4-(4-formylpiperazino)pyrimidine (2.7 g), m.p. 116° C.

Analysis %: Found: C,55.9; H,7.2; N,29.5. Calculated for C$_{11}$H$_{17}$N$_5$O: C,56.1; H,7.3; N,29.8 ii. This product (2.5 g) in methanol (31 ml) and 2N hydrochloric acid (8 ml) was stirred at room temperature for 2.25 hours and then heated on a steam bath for 2.25 hours. The solvent was evaporated in vacuo and the residue crystallized from ethanol to give 2-dimethyl-amino-4-piperazinopyrimidine, dihydrochloride, ¾ hydrate m.p. 260°–270° C.

Analysis %: Found: C, 41.0; H, 6.9; N, 24.0. Calculated for C$_{10}$H$_{17}$N$_5$.2HCl.¾H$_2$O: C, 40.9; H, 7.0; N, 23.9.

PREPARATION C

2-Hydroxy-4-piperazinopyrimidine, dihydrochloride

2-Chloro-4-(4-formylpiperazino)pyrimidine (5.0 g) in 2N hydrochloric acid (17 ml) was stirred at room temperature for 2.25 hours and then heated on a steam bath for 2.25 hours. The solvent was evaporated in vacuo and replaced by 6N hydrochloric acid (30 ml). The solution was heated on a steam bath for 2.5 hours and then evaporated in vacuo. T.L.C. indicated reaction was still incomplete and therefore the residue in concentrated hydrochloric acid (30 ml) was heated on a steam bath for 3 hours and then evaporated in vacuo. The residue crystallized from methanol to give 2-hydroxy-4-piperazinopyrimidine, dihydrochloride (2.3 g), m.p. >250° C.

Analysis %: Found: C, 37.6; H, 5.7; N, 21.9. Calculated for C$_8$H$_{12}$N$_4$O.2HCl: C, 38.0; H, 5.6; N, 22.1.

PREPARATION D

4-Chloro-6-isopropoxy-pyrimidine

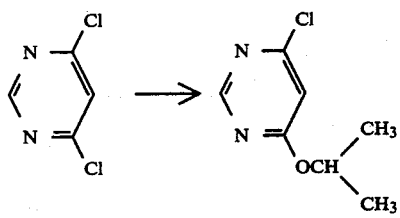

A solution of sodium isopropoxide (prepared from 0.77 g sodium) in isopropanol (230 ml) was added dropwise over 8 hours to a stirred solution of 4,6-dichloropyrimidine (5.0 g) in isopropanol (60 ml) at room temperature. The solvent was evaporated in vacuo, the residue taken up in water and extracted three times with diethylether (3×70 ml). The combined ether extracts were dried ($Na_2SO_4$) and evaporated in vacuo to give 4-chloro-6-isopropoxy pyrimidine (4.4 g) as an oil, characterized spectroscopically, and used directly.

PREPARATION E

3-Isopropoxy-6-piperazinopyridazine

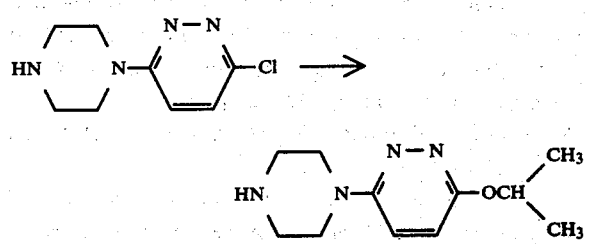

3-Chloro-6-piperazinopyridazine (4.0 g) [J. Med. Chem., 5, 541 (1963)] and sodium isopropoxide, prepared by addition of sodium (0.7 g) to dry isopropanol (70 ml), were heated in a bomb at 130°-140° C. for 10 hours. The solvent was evaporated in vacuo, the residue taken up in methylene chloride (300 ml) and the resulting solution washed with water (2×50 ml). The organic extract was dried ($Na_2SO_4$) and evaporated in vacuo to give 3-isopropoxy-6-piperazinopyridazine (3.3 g). A sample in ethyl acetate, was converted to the maleate salt by treatment with maleic acid in ethyl acetate. The resulting solid was re-crystallized from ethanol, m.p. 144°-145° C.

Analysis: Found: C,49.1; H,5.7; N,11.7 Calculated for $C_{11}H_{18}N_4O.2C_4H_4O_4.\frac{1}{2}H_2O$: C,49.2; H,5.9; N, 12.1.

PREPARATION F

Preparation of 4-(6-hydroxypyridazin-3-yl)piperazine, hydrobromide

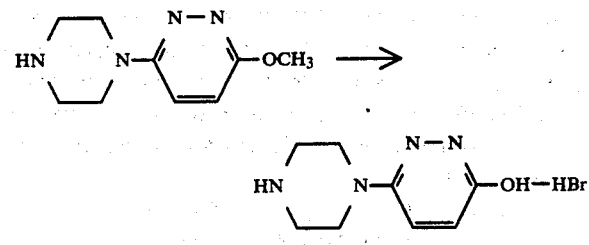

4-(6-Methoxypyridazin-3-yl)piperazine (7.2 g) (J. Med. Chem. 1963, 5, 541) in 48% hydrobromic acid (140 ml) was heated at 110°-120° for 1½ hours, left at room temperature overnight, then heated at 120° for a further 1 hour. The solvent was evaporated in vacuo and the residue treated twice with isopropanol and evaporated to dryness. The resulting solid was triturated with diethyl ether, filtered and washed with ether to give 4-(6-hydroxypyridazin-3-yl)piperazine, hydrobromide (11.2 g). A sample re-crystallized from ethanol had m.p. 289°-291°.

Analysis %: Found: C,36.8; H,5.0; N,21.4 Calculated for $C_8H_{12}N_4O.HBr$: C,36.8; H,5.0; N,21.5.

PREPARATION G

Preparation of 4,6-diethoxy-2-piperazino-1,3,5-triazine

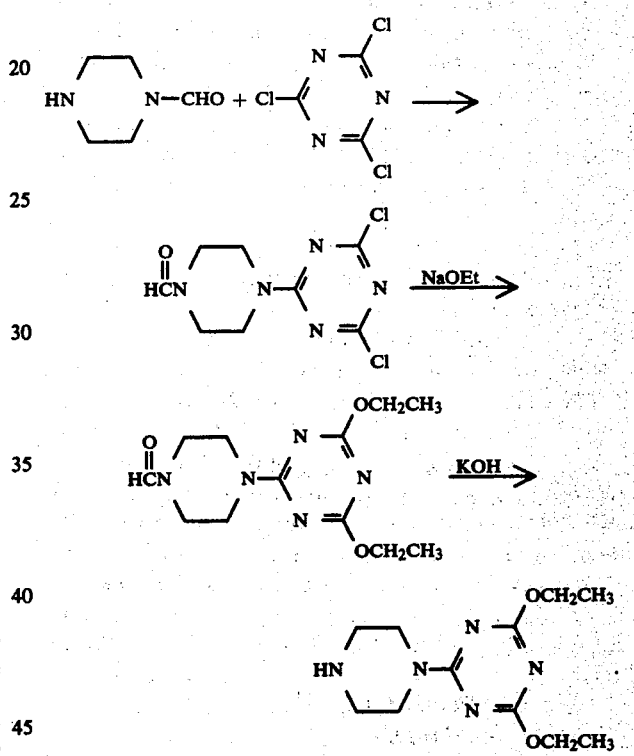

(a) 4,6-Dichloro-2-(4-formylpiperazino)-1,3,5-triazine

1-Formylpiperazine (5.0 g) in dry acetone (28 ml) was added dropwise to a stirred suspension of cyanuric chloride (6.2 g) and sodium bicarbonate (2.58 g) in dry acetone (153 ml) at −35°. The reaction mixture was stirred at −30° for 1¾ hours. Insoluble material was removed by filtration and washed with acetone. The combined filtrate and washings were evaporated in vacuo and the residue taken up in methylene chloride, filtered and the filtrate evaporated in vacuo. The resulting solid was re-crystallized twice from ethyl acetate to give in two fractions 4,6-dichloro-2-(4-formylpiperazino)1,3,5-triazine (3.1 g) m.p. 163°-165°.

Analysis %: Found: C,36.5; H,3.4; N,27.1. Calculated for $C_8H_9Cl_2N_5O$: C,36.7; H,3.5; N,26.7.

(b) 4,6-diethoxy-2-(4-formylpiperazino)-1,3,5 triazine

A solution of sodium ethoxide in dry ethanol (prepared from 1.76 g sodium in 100 ml ethanol) was added dropwise to a stirred suspension of 2,4-dichloro-6-(4-formylpiperazino)-1,3,5-triazine (10 g) in dry ethanol (740 ml). The reaction mixture was stirred at room temperature for 6 hours. The solvent was evaporated in vacuo and the residue partitioned between methylene chloride and water. The organic layer was separated, washed 3 times with water, dried (Na$_2$SO$_4$) and evaporated in vacuo to give a solid (7.2 g). Re-crystallization from ethyl acetate gave 4,6-diethoxy-2-(4-formyl-piperazino)-1,3,5-triazine (6.6 g), m.p. 106°-108.5°.

Analysis %: Found: C,51.3; H,6.8; N,24.7. Calculated for C$_{12}$H$_{19}$N$_5$O$_3$: C,51.2; H,6.8; N,24.9.

(c) 4,6-Diethoxy-2-piperazino-1,3,5-triazine

The product from (b) (3.25 g) in potassium hydroxide solution (1N, 20 ml) and ethanol (30 ml) was left at room temperature for 3 hours. Then further potassium hydroxide solution (20 ml) was added. After 45 minutes the reaction mixture was extracted with chloroform (5×30 ml), and the combined chloroform extracts dried (Na$_2$SO$_4$) and evaporated in vacuo to give 4,6-diethoxy-2-piperazino-1,3,5-triazine (3.0 g) as an oil. The product was characterized spectroscopically and used directly without further purification.

PREPARATION H

Preparation of 3-Phenoxy-6-piperazinopyridazine

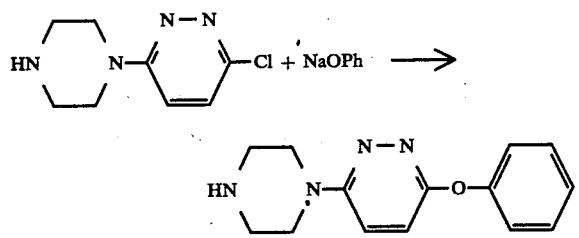

Phenol (39.8 g) was treated with a solution of sodium methoxide in methanol (prepared from 0.7 g sodium in 60 ml dry methanol) and the solvent evaporated in vacuo. 3-Chloro-6-piperazinopyridazine (4.0 g) was added to the resulting mixture of sodium phenate and phenol and the mixture heated at 125°-130° for 10 hours with stirring. Methylene chloride (200 ml) was added to the cooled reaction mixture and the solution was washed with aqueous sodium hydroxide solution (3×60 ml, 10%). The organic layer was dried (Na$_2$SO$_4$) and evaporated in vacuo. The residue was taken up in isopropanol, treated with charcoal, filtered through "Hyflo" and evaporated in vacuo. Chromatography of the residue on silica ("Keiselgel H", 15 g) eluting with chloroform gave 3-phenoxy-6-piperazinopyridazine (2.0 g). A sample re-crystallized from ethyl acetate as the hemihydrate, m.p. 96°-97°.

Analysis %: Found: C,63.1; H,6.2; N,21.4. Calculated for C$_{14}$H$_{16}$N$_4$O.½H$_2$O: C,63.4; H,6.5; N,21.1.

PREPARATION I

Preparation of 4-chloro-6-(6,7-dimethoxy-1,2,3,4-tetrahydroisoquinol-2-yl)pyrimidine Sodium hydroxide solution (80 ml, 1N) was added to a suspension of 6,7-dimethoxy-1,2,3,4-tetrahydroisoquinoline hydrochloride in water (20 ml) followed by 4,6-dichloropyrimidine (5.95 g) and the mixture was heated on a steam bath for 5 hours. The solvent was evaporated in vacuo to give a brown oil which solidified on standing. Re-crystallization from aqueous ethanol followed by isopropanol gave 4-chloro-6-(6,7-dimethoxy-1,2,3,4-tetrahydroisoquinol-2-yl)pyrimidine (6.0 g). An analytical sample re-crystallized from isopropanol, m.p. 88°-89°.

We claim:

1. A compound of the formula

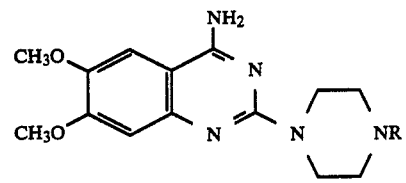

or a pharmaceutically acceptable acid addition salt thereof, wherein R is of the formula

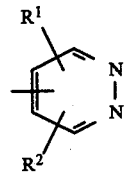

wherein R$^1$ is hydrogen and R$^2$ is 6,7-dimethoxy-1,2,3,4-tetrahydroisoquinolin-2-yl, or R$^1$ and R$^2$ are each a member selected from the group consisting of hydrogen, hydroxy, F, Cl, Br, I, (alk)R$^3$, O(alk)R$^3$, S(alk)R$^3$, NR$^4$R$^5$, C$_6$H$_4$R$^6$ and OC$_6$H$_4$R$^6$, where (alk) is (C$_1$-C$_4$)alkylene, R$^3$ is hydrogen or C$_6$H$_4$R$^6$, when taken separately, R$^4$ is hydrogen or (C$_1$-C$_4$)alkyl and R$^5$ is hydrogen, phenyl, (alk)R$^3$ or (C$_3$-C$_7$)cycloalkyl, or R$^4$ and R$^5$ taken together with the nitrogen atom to which they are attached form a pyrrolo, piperidino, 4-methylpiperazino, morpholino or thiomorpholino group and R$^6$ is hydrogen, F, Cl, Br, I, (C$_1$-C$_4$)alkyl or (C$_1$-C$_4$)alkoxy.

2. A compound according to claim 1 wherein R is

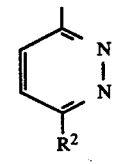

3. A compound according to claim 2 wherein R$^2$ is hydrogen, hydroxy, F, Cl, Br, (alk)R$^3$, O(alk)R$^3$, NR$^4$R$^5$, C$_6$H$_4$R$^6$ or OC$_6$H$_4$R$^6$.

4. A compound according to claim 3 wherein R$^2$ is hydrogen, hydroxy, Cl, N(CH$_3$)$_2$, OC$_6$H$_5$, OCH$_3$, OCH(CH$_3$)$_2$ or C$_6$H$_5$.

5. A compound according to claim 4 wherein R$^2$ is hydrogen or OCH(CH$_3$)$_2$.

6. The compound according to claim 5 wherein R$^2$ is hydrogen.

7. The compound according to claim 5 wherein R$^2$ is OCH(CH$_3$)$_2$.

8. A method for treating mammalian hypertension which comprises orally or parenterally administering to a mammal in need of such treatment an antihypertensive effective amount of a compound according to claim 1.

9. A pharmaceutical composition for oral or parenteral administration to a mammal comprising a pharmaceutically acceptable carrier and an antihypertensive effective amount of a compound according to claim 1.

* * * * *